United States Patent

Baum

[11] Patent Number: 5,972,981
[45] Date of Patent: *Oct. 26, 1999

[54] BIOCIDAL 3-ISOTHIAZOLINONE COMPOSITIONS

[75] Inventor: Rüdiger Baum, Waghäusel, Germany

[73] Assignee: Thor Chemie GmbH, Germany

[ * ] Notice: This patent is subject to a terminal disclaimer.

[21] Appl. No.: 08/959,950

[22] Filed: Apr. 30, 1997

Related U.S. Application Data

[63] Continuation-in-part of application No. 08/751,223, Nov. 15, 1996, Pat. No. 5,824,695.

[30] Foreign Application Priority Data

Nov. 17, 1995 [EP] European Pat. Off. ............ 951 18 145

[51] Int. Cl.⁶ .................................................. A01N 43/80
[52] U.S. Cl. ............................................................. 514/372
[58] Field of Search ............................................... 514/372

[56] References Cited

U.S. PATENT DOCUMENTS

| | | | |
|---|---|---|---|
| 3,849,430 | 11/1974 | Lewis et al. | 106/18.32 |
| 3,870,795 | 3/1975 | Miller et al. | 424/270 |
| 5,068,338 | 11/1991 | Bayer et al. | 548/101 |
| 5,312,827 | 5/1994 | Bayer et al. | 514/372 |
| 5,824,695 | 10/1998 | Baum | 514/372 |

*Primary Examiner*—Kevin E. Weddington
*Attorney, Agent, or Firm*—Hedman, Gibson & Costigan, P.C.

[57] ABSTRACT

There is provided a method for the production of improved biocidal compositions which comprise at least one 3-isothiazolinone of the general formula

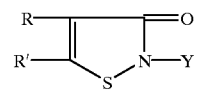

Y is a hydrogen atom or an unsubstituted alkyl radical having 1 to 18 carbon atoms, a cylo alkyl radical having 5 to 8 carbon atoms, an aralkyl radical having 7 to 11 carbon atoms or an aryl radical having 6 to 10 carbon atoms and R and R' are in each case a hydrogen atom or halogen atom or a $C_1$ to $C_4$-alkyl radical, or, when taken together, R and R' contain an alkylene group to form a hydrocarbon ring, the 3-isothiazolinone being produced in known manner and then stabilized by the addition of a nitrate. The method is characterized by the fact that the mixture obtained upon the production of the 3-isothiazolinone is subjected to an additional stabilization after the addition of the nitrate by storing it at a pH of 0.2 to 2.0 and a temperature of at most 40° C. for a period of at least 2 days and then again neutralized to a higher pH in the range of 2.5 to 3.5.

8 Claims, No Drawings

BIOCIDAL 3-ISOTHIAZOLINONE COMPOSITIONS

CROSS-REFERENCE TO RELATED APPLICATION

This patent application is a continuation-in-part of patent application Ser. No. 08/751,223, filed Nov. 15, 1996, now U.S. Pat. No. 5,824,695.

BACKGROUND OF THE INVENTION

Biocides are an indispensable part of numerous chemical mixtures of substances and of materials in everyday use both in the industrial and the non-industrial area. The biocides prevent that said mixtures of substances and materials spoil due to the action of microorganisms and thereby become useless. At the same time, they thus also protect the health of the consumer.

Biocides are necessary for the preservation of, for instance, cleaning agents, scouring agents, detergents, polishing agents, coating agents, adhesives, plasters, paper, cardboard, textiles, leather, drilling fluids, metal-working fluids, latex emulsions, plastics, fuels and water in cooling circuits. The intended effect of the biocides imparts the substrates to which it has been admixed, a substantially longer life, both in the closed container during storage and transportation and during the use of the substrates.

3-isothiazolinones are important biocidally active substances which incorporate the most important properties of a modern biocide. Mention must be made especially of the very wide spectrum of activity against bacteria, mold fungi, yeasts and algae and of the easy degradability in the environment. Depending on the substituents in the isothiazolinone molecule, the isothiazolinones differ in their reactivity and thus also in their action and/or they differ with respect to their solubility.

The production of 3-isothiazolinones is known and can take place in various manners. In U.S. Pat. No. 3,849,430, two general methods or processes are disclosed for the preparation of 3-isothiazolinones. In accordance with the first alternative, a dithiodiamide is converted to the corresponding 3-isothiazolinone by cyclization with a halogen agent. There is thus produced, for instance, from 3,3'-dithio-N,N'-dimethyldipropionamide by reaction with sulfurylchloride a mixture of 5-chloro-2-methyl-3-isothiazolinone and 2-methyl-3-isothiazolinone. In accordance with the second alternative, a mercaptoamide is used instead of the dithiodiamide. In this case, one obtains, for instance by reacting N-methyl-3-mercaptopropionamide with elementary chlorine, also a mixture of the two above-mentioned 3-isothiazolinones.

For many applications, it is necessary to formulate the 3-isothiazolinone in solutions. As solvent, there is preferably employed water, but polar organic solvents, such as alcohols, are also used for this purpose. Some of these 3-isothiazolinone solutions can exhibit chemical decomposition of the 3-isothiazolinones already during their storage, i.e. prior to their intended use, which results in a reduction of the biocidal action.

In accordance with U.S. Pat. No. 3,870,795, this disadvantage can be counteracted by adding metal nitrates or metal nitrites for the chemical stabilization of the 3-isothiazolinones in formulations. It was found, however, that this type of stabilization is not sufficient in the case of some 3-isothiazolinones which are particularly susceptible to decomposition. It is, namely, possible that there occur precipitations and losses of active ingredients which can greatly impair the use of the solutions. This can be reduced by subjecting such nitrate-stabilized 3-isothiazolinone solutions to an additional stabilization. In accordance with EP-B-95907, this takes place, in the case of a mixture of 5-chloro-2-methyl-3-isothiazolinone and 2-methyl-3-isothiazolinone, by heat treatment for four hours at 95° C. In connection with the beneficial effect of heat treatment at 95° C. mention is also made of U.S. Pat. No. 5,068,338 and U.S. Pat. No. 5,312,827.

It has, however, been found that this heat treatment also leads to disadvantages.

On the one hand, the relatively high temperature upon the heat treatment of the 3-isothiazolinone solution has the effect that certain impurities, which were produced as by-products upon the production of the isothiazolinone and are still present in the solution, are nitrosated by the nitrate added as stabilizer to form nitrosamines. The latter, however, are carcinogenic substances which must be avoided under all circumstances. Said by-products occur primarily upon the production of the isothiazolinone from the corresponding dithiodiamide. In addition, however, the relatively high temperature of the heat treatment results in the partial decomposition of the valuable 3-isothiazolinone, regardless of which process is used, leading to the formation of colored impurities and subsequent loss of active ingredient. Thus, the quality of the 3-isothiazolinone product produced is substantially impaired.

SUMMARY OF THE INVENTION

The primary object of this invention is to provide 3-isothiazolinone compositions with improved stability, greater purity and less color. The stabilization method used in this invention leads no losses or only slight losses of active ingredient, and the solutions obtained have a reduced content of harmful by-products, the presence of which can also be indicated in the form of precipitations and colorations of the compositions.

The invention achieves these objects by providing a method for the production of improved biocidal or biostatic compositions present in water and/or in a polar organic solvent and containing at least one 3-isothiazolinone of the general formula

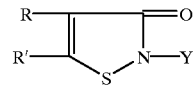

in which Y is a hydrogen atom or an unsubstituted alkyl radical having 1 to 18 carbon atoms, a cycloalkyl radical having 5 to 8 carbon atoms, an aralkyl radical having 7 to 11 carbon atoms or an aryl radical having 6 to 10 carbon atoms and R and R' are in each case a hydrogen atom or halogen atom, a $C_1$ to $C_4$ alkyl radical, or R and R', taken together, contain an C1 to C4 alkylene group to form a hydrocarbon ring, the 3-isothiazolinone being prepared in a manner known per se and then stabilized by the addition of a nitrate, characterized by the fact that the mixture obtained upon the production of the 3-isothiazolinone is subjected, after the addition of the nitrate, to an additional stabilization by storing it at a pH of from about 0.2 to about 2.0 and a temperature of a maximum of about 40° C. for a period of at least 2 days (48 hours) and thereupon again neutralizing the composition to a pH of from about 2.5 to about 3.5.

DETAILED DESCRIPTION OF THE INVENTION

An alcohol such as a glycol, for instance diethylene glycol, dipropylene glycol and 1,2-propylene glycol, may be present as polar organic solvent in the composition of invention.

The concentration of 3-isothiazolinone in the composition of the invention may vary within a wide range, for instance within a range from 1 to 30% by weight, preferably from 10 to 20% by weight.

The improved composition of this invention is obtained by treatment of the mixture obtained from the production process of the 3-isothiazolinone with a metal nitrate and subjecting it to the following stabilization storage conditions: (i) a pH in the range of 0.2 to 2.0, preferably 0.5 to 1.5, and most preferably 0.8 to 1.2; (ii) a temperature in the range of 0° C. to 40° C., preferably 10° C. to 30° C.; (iii) for a period of two days to four weeks, preferably one week to two weeks.

Following the above stabilization storage treatment, the composition is then further neutralized to a pH in the range of from 2.5 to 3.5.

The method of the invention is particularly advantageous upon its application to mixtures which contain 5-chloro-2-methyl-3-isothiazolinone and/or 2-methyl-3-isothiazolinone. This invention, however, may also be applicable to 3-isothiazolinone compositions containing 2-n-octyl-3-isothiazolinone, 4,5-dichloro-3-isothiazolinone, 4,5-dichloro-2-cyclohexyl-3-isothiazolinone and 4,5-trimethylene-2-methyl-3-isothiazolinone. (The latter may be found in U.S. Pat. No. 4,708,959).

The method of the invention can, however, also successfully be used in the case of compositions of other 3-isothiazolinones.

The application of the method of the invention is independent of the manner of production of the 3-isothiazolinone. The active ingredient can, therefore, have be obtained for example by the cyclization of a dithioamide or a mercaptoamide or some other known manner.

The method of the invention stabilizes 3-isothiazolinone solutions without it being necessary to carry out the previously customary heat treatment at relatively high temperatures. The method of the invention thus has the advantage that it entails no losses or only slight losses of active ingredient.

Since the decomposition of the 3-isothiazolinone upon the additional stabilization treatment according to the invention is avoided, the formation of corresponding decomposition products is also prevented. This means that the compositions produced in accordance with the invention contain on the whole less impurities than the corresponding known compositions after their heat treatment.

The greater purity of the compositions obtained in accordance with the invention is also reflected in their appearance. Even after lengthy storage, the solutions are substantially or completely clear because they are almost or completely free of precipitates. In contrast thereto, the known heat-treated solutions form during their storage a sediment unless they are mixed with additional stabilizers, for instance with copper salts.

The color of the compositions produced in accordance with the invention also reflects the improved purity. The compositions are almost or completely colorless, while the known heat-treated compositions are strongly colored.

Finally, compared with the known heat treatment (at almost 100° C.), the method of the invention naturally leads to a saving in energy, since a substantially lower temperature, for instance room temperature, is sufficient for the invention.

The method of the invention is suitable in particular for the stabilizing of 3-isothiazolinones which, due to their method of manufacture, still contain production-induced impurities.

After the additional stabilization in accordance with the invention in the pH range and temperature range indicated and for the duration indicated, the pH of the 3-isothiazolinone solution is increased again. This final pH value depends on the application for which the solution is to be introduced on the market.

DESCRIPTION OF THE PREFERRED EMBODIMENT

The invention will be explained by way of the following examples.

All contents of active ingredient indicated below were measured by means of high pressure liquid chromatography (HPLC). Quantities indicated in percent refer to the weight. The storing of the samples took place in airtight glass vessels.

EXAMPLE OF MANUFACTURE

As starting material, there was produced an aqueous compound which contained as active ingredient a mixture of 5-chloro-2-methyl-3-isothiazolinone and 2-methyl-3-isothiazolinone. The two 3-isothiazolinones were obtained in known manner in accordance with U.S. Pat. No. 3,849,430. For this purpose N-methyl-3-mercaptopropionamide was cyclized with elementary chlorine in butyl acetate as solvent with the formation of 2-methyl-3-isothiazolinone (MIT) and 5-chloro-2-methyl-3-isothiazolinone (CIT).

The hydrochlorides of the above products were removed by filtration and taken up in water.

The solution obtained then contained the following quantity percentages:

6.3% MIT 17.3% CIT

This solution was brought to a pH of 0.9 by means of an aqueous magnesium oxide slurry under cooling at a temperature of 25 to 27° C. and then mixed with magnesium nitrate for stabilization.

The solution obtained had a pH of 0.9 and was clear and almost colorless. It contained the following substances:

3.98% MIT 10.91% CIT 15.80% magnesium nitrate 5.50% magnesium chloride

This solution served as starting material for the following example and for comparison examples 1 to 3.

EXAMPLE 1

A part of the solution present at the end of the manufacturing example was subjected to additional stabilization at 25° C. by storage at a pH of 0.9 and a temperature of 25° C. for 2 weeks, then brought to a pH of 2.9 with magnesium oxide and filtered.

The contents of active ingredients, the color index (according to Gardner) and the appearance of the solution obtained in this manner immediately after the 2-week stabilization treatment are indicated in Table I below.

The stability of this solution after storage for two weeks at 54° C. and alternatively for 3 months at 20° C. can be noted from Table II.

The solution was furthermore diluted with water to a commercially customary concentration of 1.5% isothiazolinone.

The stability of this diluted solution results are in Table III.

In Table I, the loss of the active ingredient refers only to CIT. In this connection, 100% CIT (without loss of active ingredient) correspond to the quantitative portion of 10.91% CIT indicated in the manufacturing example for the starting solution. It is sufficient to consider in this case only the CIT (and not also the MIT) since the CIT is substantially more active as biocidal active ingredient than the MIT and also represents that component in the MIT/CIT mixture which requires special stabilization.

For the same reason, in Table II the residual percentage of the isothiazolinone in the solution stored also refers only to the CIT.

EXAMPLE 2

In accordance with Example 1, a part of the solution present at the end of the manufacturing example was subjected to additional stabilization at 25° C. by storage at a pH of 1.3, instead of 0.9, and a temperature of 25° C. for 3 weeks, instead of 2 weeks, then brought to a pH of 2.8, instead of 2.9, with magnesium oxide and filtered.

The contents of active ingredients, the color index, appearance and stability of the solution were determined in the same manner as in the preceding example. The results of Testing are set forth in Tables I, II, and III, respectively.

COMPARISON EXAMPLE 1

This comparison example illustrates the stabilization method described in U.S. Pat. No. 3,870,795, i.e. the addition of a nitrate without further additional stabilization.

A part of the solution present at the end of the manufacturing example was not subjected to any further stabilization treatment, but was brought immediately after the production to a pH of 2.9 with magnesium oxide and filtered.

The contents of active ingredients, the color index, the appearance and the stability of the solution were determined in the same way as in the preceding example. The results are set forth in corresponding manner in Tables I, II and III.

COMPARISON EXAMPLE 2

In this comparison example, the stabilization method described in EP-B-95907 or U.S. Pat. No. 5,312,827 was employed, i.e. the stabilization took place by the addition of a nitrate and by a subsequent heat treatment as additional stabilization.

A part of the solution present at the end of the manufacturing example was brought immediately after its production to a pH of 2.9 with magnesium oxide, then heated for four hours to 95° C. for further stabilization and then cooled to room temperature and filtered.

The contents of active ingredients, the color index, appearance and stability of the solution were determined in the same way as in the preceding examples. The results are set forth in corresponding manner in Tables I, II and III.

COMPARISON EXAMPLE 3

This comparison example corresponds substantially to comparison example 2 with the difference that the stabilization by heat treatment was effected at a lower pH value.

A part of the solution present at the end of the manufacturing example was heated immediately after its production for 4 hours to 95° C. for stabilization, and then brought to a pH of 2.9 with magnesium oxide and filtered.

The contents of active ingredients, the color index, appearance and stability of the solution were determined in the same manner as in the preceding example. The results are set forth in corresponding manner in Tables I, II and III.

It is evident from comparison examples 1 to 3 that the stabilization with magnesium nitrate alone leads to an only slightly colored by not very stable product. While the heat treatment at 95° C. improves the stability, it results in a definite discoloration and in losses of active ingredient. Contrary thereto, the examples of the invention lead neither to significant losses of ingredient nor to discolorations and in addition to this, the final product exhibits improved stability.

TABLE I

Comparison of the solutions immediately after their production % loss of CIT conc. after addnl. stablzn.

|  | MIT % | CIT % | treatment % | Color Index (Gardner) | Appearance |
|---|---|---|---|---|---|
| Example 1 | 3.94 | 10.85 | 0.6 | 1–2 | Clear, almost colorless |
| Example 2 | 3.95 | 10.86 | 0.5 | 1–2 | Clear, nearly colorless |
| Comparison Example 1 | 3.98 | 10.91 | 0.0 | 1–2 | Clear, almost colorless |
| Comparison Example 2 | 3.87 | 10.15 | 6.9 | 5 | Clear, yellow-amber color |
| Comparison Example 3 | 3.73 | 10.22 | 6.3 | 6 | Clear, yellow-amber color |

TABLE II

Stability of isothiazolinone solutions

|  | Residue of CIT after storage 14 days/54° C. % | Appearance of solution after storage 3 mos./20° C. | Color index (Gardner) after storage 3 mos./20° C. |
|---|---|---|---|
| Example 1 | 98.5 | + | 1–2 |
| Example 2 | 98.6 | + | 1–2 |
| Comparison Example 1 | 85.3 | – | 2 |
| Comparison Example 2 | 98.8 | o | 5 |
| Comparison Example 3 | 98.2 | o | 6 |

+ = clear, without sediment
o = slightly cloudy with sediment
– = cloudy with sediment

TABLE III

Stability of the 1.5% isothiazolinone solutions

|  | Appearance of the solution after storage | | |
|---|---|---|---|
|  | 3 days/ 20° C. | 14 days/ 20° C. | Color |
| Example 1 | + | + | colorless |
| Example 2 | + | + | colorless |
| Comparison Example 1 | o | o | colorless |
| Comparison Example 2 | o | – | yellow |
| Comparison Example 3 | o | – | yellow |

+ = clear, without sediment
o = slightly cloudy with sediment
– = cloudy with sediment The foregoing Examples illustrate the invention, but are not to be construed to limit the following claims. All obvious variations are within the full intended scope of the claims.

I claim:

1. A method for the production of improved biocidal compositions which contain at least one 3-isothiazolinone of the general formula:

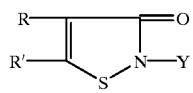

in which Y is a hydrogen atom or an unsubstituted alkyl radical having 1 to 18 carbon atoms, a cylo alkyl radical having 5 to 8 carbon atoms, an aralkyl radical having 7 to 11 carbon atoms or an aryl radical having 6 to 10 carbon atoms and R and R' are in each case a hydrogen atom or halogen atom or a $C_1$ to $C_4$-alkyl radical, or, when taken together, R and R' contain an alkylene group to form a hydrocarbon ring, the 3-isothiazolinone being produced in a manner known per se and then stabilized by the addition of a nitrate, said method characterized by the fact that the mixture obtained upon the production of the 3-isothiazolinone is subjected, after the addition of the nitrate, to an additional stabilization by storing it at a pH of 0.2 to 2.0 and a temperature of from 0° C. to 40° C. for a period of at least 2 days and thereupon bringing it again to a higher pH in the range of 2.5 to 3.5.

2. A method according to claim 1, characterized by the fact that the additional stabilization takes place at a pH of 0.5 to 1.5 and a temperature of 10 to 30° C. for a period of 1 to 2 weeks.

3. A method according to claim 1, characterized by the fact that the additional stabilization takes place at a pH of 0.8 to 1.2 and a temperature of 10 to 30° C. for a period of 1 to 2 weeks.

4. A method according to claim 1, characterized by the fact that as 3-isothiazolinone there is used 5-chloro-2-methyl-3-isothiazolinone and/or 2-methyl-3-isothiazolinone.

5. An improved biocidal 3-isothiazolinone composition prepared by the method of claim 1.

6. An improved biocidal 3-isothiazolinone composition prepared by the method of claim 1, characterized by the fact that the additional stabilization takes place at a pH of 0.5 to 1.5 and a temperature of 10 to 30° C. for a period of 1 to 2 weeks.

7. An improved biocidal 3-isothiazolinone composition prepared by the method of claim 1, characterized by the fact that the additional stabilization takes place at a pH of 0.8 to 1.2 and a temperature of 10 to 30° C. for a period of 1 to 2 weeks.

8. An improved biocidal 3-isothiazolinone composition prepared by the method of claim 1, characterized by the fact that as 3-isothiazolinone there is used 5-chloro-2-methyl-3-isothiazolinone and/or 2-methyl-3-isothiazolinone.

* * * * *